United States Patent [19]

Hewitt

[11] Patent Number: 4,900,677
[45] Date of Patent: Feb. 13, 1990

[54] PROCESS FOR RAPID ISOLATION OF HIGH MOLECULAR WEIGHT DNA

[75] Inventor: Peter L. Hewitt, Andover, Mass.

[73] Assignee: E. I. Du Pont de Nemours and Company, Wilmington, Del.

[21] Appl. No.: 911,808

[22] Filed: Sep. 26, 1986

[51] Int. Cl.$^4$ .......................... C12N 1/06; C12N 1/08
[52] U.S. Cl. ......................................... 435/259; 435/6; 435/264; 435/267; 435/270
[58] Field of Search ............... 435/270, 259, 264, 267, 435/6; 536/27

[56] References Cited

U.S. PATENT DOCUMENTS 4,481,294 11/1984 Downs ................................. 435/267
4,483,920 11/1984 Gillespie et al. ........................ 435/6

OTHER PUBLICATIONS von Hippel et al., Science, 145:577–580 (1964).
Chassy et al., App. Env. Microb., 39(1):153–158 (1980).
de Kloet, J. Microb. Methods, 2:189–196 (1984).
Methods in Enzymology, Academis Press, N.Y. 1980), vol. 65, pp. 118–125.
Bresser et al, DNA, 2(3):243–254, "Quick-Blot: Selective RNA or DNA Immobilization from Whole Cells" (1983).
Marmur, Journal of Molecular Biology, 3, 208–218 (1961).
Carter et al., Biotechniques, 1(3), 142–147 (1983).
Gross–Bellard et al., European Journal of Biochemistry, 36, 32–38 (1973).
Monsen et al., FEMS Microbiology Letters, 16, 19–24 (1983).
Potter et al., Cancer Letters, 216, 335–341 (1985).

*Primary Examiner*—Esther M. Kepplinger
*Attorney, Agent, or Firm*—George A. Frank

[57] ABSTRACT

A procedure for isolating high molecular weight nucleic acids utilizing a mixture of lytic enzymes and a chaotropic agent to complete protein denaturation and dissociation from nucleic acids is provided. The nucleic acids so obtained are useful for restriction enzyme analysis and DNA probe hybridization.

8 Claims, No Drawings

PROCESS FOR RAPID ISOLATION OF HIGH MOLECULAR WEIGHT DNA

TECHNICAL FIELD

This invention relates to the field of molecular biology and more particularly to the isolation of high molecular weight DNA suitable for restriction enzyme analysis.

BACKGROUND ART

There have been great advances in molecular biology in recent years in terms of new restriction enzymes, improved DNA cloning methods, improved hybridization probes, and improved hybridization supports: however, little, if any, attention has been paid to preparation of the samples for use in these procedures. That is, little has been done to improve the speed and efficiency of isolation and preparation of nucleic acids, specifically DNA, for use in these procedures.

The classic reference for isolation of high molecular weight DNA is Marmur [Journal of Molecular Biology, Volume 3, 208–218 (1961)]. The process taught by Marmur includes 14 steps, some of which must be repeated to insure completeness. Many of these steps are time consuming and most require a highly skilled technician to assure successful isolation of the DNA. The individual steps are discussed below showing all details provided by the author:

1. Cell lysis

A cellular suspension is first treated with a detergent, sodium dodecyl sulfate, at 60° C. in an attempt to lyse the cells. If lysis is achieved, one proceeds to the next step; if not, an enzyme, lysozyme, is added and allowed to digest the cells for 30–60 minutes. These steps can be reversed but, if they are, the detergent must be added for the subsequent processes to work correctly. This method of cell lysis, while broadly effective, is not universally so. There are organisms with cell walls which are resistant to both lysozyme and detergent treatment (e.g. Streptococcus pyogenes).

2. Deproteinization

The viscous lysed suspension is made 1M in perchlorate and extracted with a chloroform-isoamyl alcohol mixture. This mixture is then centrifuged to form 3 layers, the middle layer containing the proteins. The upper aqueous layer contains the nucleic acids and is removed for further processing.

3. Nucleic acid precipitation

The nucleic acids are precipitated by layering ethanol on top of the aqueous layer and collecting them on a glass rod. The precipitate is drained of excess ethanol by pressing the precipitate against the side of the flask. This step requires a highly skilled technician because, as is the case with all DNA precipitation steps to follow, significant losses of the desired DNA can occur. These losses occur due to incomplete precipitation, redissolution of precipitate during washing, and binding of precipitating DNA to the walls of the vessel.

4. Dissolution of nucleic acids

The precipitate is transferred to dilute saline-citrate buffer and the nucleic acid is redissolved by gentle stirring. Excessive stirring causes shearing of the DNA resulting in low molecular weight DNA being formed and, therefore, great care must be exercised.

5. Deproteinization

The soluble nucleic acids are re-extracted as described in Step 2 to remove any remaining proteins. This step may be repeated several times to assure complete removal of the proteins. Complete removal is assumed when very little protein is seen at the interface of the solvent layers.

6. Nucleic acid precipitation

Step 3 is repeated to purify further the nucleic acids.

7. Dissolution of nucleic acids

Step 4 is repeated to obtain a nucleic acid solution for further processing.

8. Ribonuclease treatment

The mixture of nucleic acids present in the solution is treated with ribonuclease for 30 minutes at 37° C. to digest any RNA present in the sample. Following digestion, it is possible to remove proteins which were resistant to earlier extractions (steps 2 and 5).

9. Deproteinization

Step 2 is repeated to obtain DNA free of RNA, any proteins released by the ribonuclease treatment, and ribonuclease itself.

10. DNA precipitation

DNA is precipitated as described in step 3.

11. Dissolution of DNA

DNA is redissolved as described in step 4.

12. Isopropyl alcohol precipitation

To the DNA solution is added an acetate-EDTA buffer and the solution is mixed rapidly. While the solution is being mixed, 0.54 volume of isopropyl alcohol is added dropwise into the vortex. Then, according to the author, "DNA usually precipitates in a fibrous form after first going through a gel phase at about 0.5 vol(umes) isopropyl alcohol"—another difficult step.

13. Isopropyl alcohol precipitation

Steps 4 and 12 can be repeated "if the yield is good".

14. Final washing

The final precipitate is washed free of acetate and salt by gently stirring the adhered precipitate in aqueous ethanol containing progressively increasing (70–95%) portions of ethanol. The DNA is then available for dissolution in the buffer of choice for use in further analysis.

The process described by Marmur and followed to date by molecular biologists is complex and prone to loss of the desired DNA. According to Marmur, recovery of up to 50% of the DNA from the cells can be achieved by carefully following this process, not a very high yield. This process also generally requires 1 to 2 days, an undesirably lengthy processing period. Furthermore, according to Marmur, it would be very difficult to devise a technique for the efficient isolation of DNA from a wide variety of microorganisms. Although Marmur's method is effective against various organisms including almost all Gram negative organisms and many Gram positive organisms, one organism of great interest, Streptococcus pyogenes is not lysed by this method. This organism is the causative agent for the common illness, strep throat.

An alternative procedure for isolating DNA also disclosed by Marmur utilizes cesium chloride centrifugation. This process, while having many fewer steps, requires centrifugation for 3 days and, therefore, is also not a rapid method for isolating DNA. Additionally, cesium ions have a detrimental effect on the biological activity of the recovered DNA.

Carter et al. [Biotechniques, Volume 1(3), 142–147 (1983)] disclose an improved isopycnic centrifugation medium which uses cesium trifluoroacetate instead of cesium chloride. The cesium trifluoroacetate is used in a fashion similar to cesium chloride. The trifluoroacetate anion, however, imparts properties to cesium trifluoroacetate that result in higher quality nucleic acid preparations when compared to traditional cesium density gradient media. The use of cesium trifluoroacetate has extended the application of isopycnic centrifugation in nucleic acid separations and purifications but the procedure is still inherently time consuming and labor intensive.

Gross-Bellard et al. [European Journal of Biochemistry, Volume 36, 32–38 (1973)] disclose a similar method useful for isolating high molecular weight DNA from mammalian cells. In this method, Proteinase K and a detergent, sodium dodecyl sulfate (SDS), are used to lyse the cells. This method is also applicable to microorganisms susceptible to these lysis conditions. Deproteinization is accomplished using phenol saturated buffers rather than chloroform:isoamyl alcohol. The use of phenol, however, requires a 4-hour dialysis to remove it before proceeding further. Any RNA present is digested using ribonuclease and then the ribonuclease is digested using proteinase K and SDS. The DNA is then deproteinized twice more and dialyzed again. Finally, the DNA is precipitated with ethanol. This procedure offers little advantage over that of Marmur. There are fewer DNA precipitations, but the procedure introduces two long dialysis steps.

Chassy et al. [Applied and Environmental Microbiology, Volume 39(1), 153–158 (1980)] disclose a procedure for extending the usefulness of lysozyme in lysing microorganisms. This procedure depends upon growing the organism in a modified medium, particularly one containing L-threonine. This leads to organisms with weakened cell wall crosslinks which are susceptible to lysozyme treatment. This procedure is useful only when the organism to be lysed is known to grow in the modified medium and precludes any possibility of using DNA collected directly from a clinical specimen without culturing the organism. Therefore, this procedure is not of general utility.

Potter et al. [Cancer Letters, Volume 26, 335–341 (1985)] disclose a method for rapid extraction and purification of DNA from human leukocytes. This method includes detergent lysis of the cells, potassium acetate precipitation of cellular material, ribonuclease digestion, adsorption chromatography using DEAE-cellulose to purify the DNA, and ethanol precipitation of the DNA. This method is applicable only to those microorganisms susceptible to detergent lysis, generally the Gram negative organisms.

Potter et al.'s method is different from Marmur's in the use of potassium acetate to precipitate the cellular contents and the use of adsorption chromatography. These authors acknowledge that DNA can be lost in the potassium acetate precipitation step. Also, as with many precipitation methods, the sample must be centrifuged in order to assure complete recovery of the precipitate and centrifugation requires expensive equipment and valuable time. Avoidance of precipitation and centrifugation steps would be advantageous.

The use of adsorption chromatography to purify DNA can also have certain disadvantages since DNA with the highest molecular weight tends to bind most strongly to the support and, therefore, is not easily eluted from the column. This can result in selective loss of the highest molecular weight DNA.

De Klowet [Journal of Microbiological Methods, Volume 2, 189–196 (1984)] discloses a method for rapid isolation of high molecular weight RNA and DNA from yeast through the use of a single glucanase enzyme, lyticase, isolated from *Oerskovia xanthineolytica*, in the presence or absence of a detergent to lyse the cells. After lysing, the sample is deproteinized by extraction with an equal volume of a phenol:chloroform (4:1) solution. The mixture is centrifuged to separate the layers and the aqueous nucleic acid-containing phase is collected. This phase is made 0.3M in sodium acetate (pH 5.0) and the nucleic acids precipitated with two volumes of ethanol. Alternatively, high molecular weight RNA can be isolated by selective precipitation with lithium chloride. The high molecular weight DNA can be isolated from the supernatant of that precipitation or directly from the previously precipitated nucleic acids. In the former case, DNA isolation proceeds with ribonuclease treatment to destroy the RNA present. DNA is then deproteinized again by phenol:chloroform extraction and precipitated with ethanol. This overall procedure is very similar to that of Marmur in that it entails repeated deproteinization with organic solvents and repeated precipitation with ethanol, both of which are undesirable. These types of treatments are undesirable in that they require skilled technicians, extensive equipment and facilities and take substantial amounts of time.

Monsen et al. [FEMS Microbiology Letters, volume 16, 19–24 (1983)] disclose a general method for cell lysis and preparation of DNA from streptococci. This method uses the lytic enzyme mutanolysin (endo-N-acetylmuraminidase) isolated from *Streptomyces globisporus* 1829 to lyse the organism. As noted above, these organisms are resistant to lysozyme and detergent-induced lysis. Monsen et al. also showed that streptococci are resistant to a general protease, Proteinase K. High molecular weight DNA was isolated by Monsen et al. using cesium chloride centrifugation. As noted above, this is a very time consuming procedure not appropriate for routine preparation of clinical samples.

None of the methods discussed offers a completely general method for lysis of microorganisms of interest in clinical diagnostic applications and isolation of their DNA. In general, these methods utilize a single enzyme and/or a detergent to lyse a limited group of organisms.

Gillespie et al. (U.S. Pat. No. 4,483,920, issued Nov. 20, 1984) disclose the immobilization onto filters of messenger RNA in the presence of a high concentration (80%) of a chaotropic salt, sodium iodide. Here the chaotropic salt is used to denature proteins, to dissociate them from mRNA and to solubilize substantially all cellular components to allow them to pass through the hybridization filter.

Von Hippel et al., Science Volume 145, 577–580 (1964), studied the denaturation of proteins and nucleic acids with chaotropic salts and found that proteins are more susceptible to such denaturation than nucleic acids. One can conclude from such findings that it might be possible to select concentrations of chaotropic salts which will denature proteins, thus aiding their dissociation from nucleic acids, without denaturing double stranded high molecular weight DNA.

There remains a need for a rapid, efficient and simple process for isolating high molecular weight nucleic acids from a wide variety of sources.

DISCLOSURE OF THE INVENTION

A method of isolating high molecular weight nucleic acids from their source organism comprising the steps of:

(A) forming a suspension of said organism containing or suspected of containing the desired nucleic acid;

(B) treating said organism with at least one lytic enzyme;

(C) treating said organism with surfactant prior to, simultaneously with or subsequent to step (B);

(D) degrading unwanted classes of nucleic acids by treatment with nucleases specific for the unwanted nucleic acids;

(E) degrading proteins by digestion with at least one broadly active protease;

(F) denaturing remaining proteins and dissociating them from the nucleic acid by adding at least one chaotropic agent; and (G) dialyzing and concentrating the nucleic acid.

DESCRIPTION OF THE INVENTION

As discussed above, there is a need for an improved method of isolating nucleic acids, particularly DNA, from their source organism. By source organism is meant any organism which contains a nucleic acid, including cells, particularly microbial cells, viruses, and mycoplasma. The cells subjected to this process include cells of mammalian or bacterial origin or a mixture of mammalian and bacterial cells. This improved method allows rapid, high yield recovery of high molecular weight nucleic acids from a wide variety of source organisms especially from most clinically relevant cell types. Surprisingly, it has been found that the method of this invention allows isolation of high molecular weight nucleic acids from a very wide variety of organisms in approximately 90 minutes. This method is expected to find the greatest utility in the isolation of DNA, but is also useful in isolating RNA.

For sake of convenience, the process will be described as being carried out with a suspension of cells but it should be understood that other nucleic acid-containing source organisms can be treated similarly. As a practical matter, it is convenient to begin this process of isolation with a cell suspension containing $1 \times 10^7$ to $1 \times 10^8$ cells in 500 $\mu$L buffer. A variety of buffers can be used, including sodium borate and sodium phosphate, but tris(hydroxymethyl)aminomethane hydrochloride (Tris) is preferred. The preferred buffer concentration is 10 mM, although a concentration from about 1 mM to about 500 mM is acceptable. The preferred pH is about 8 although a pH ranging from about 4 to about 9 is acceptable. The buffer can also contain 1-500 mM sodium chloride with 10 mM being preferred and, similarly, about 1-10 mM ethylenediaminetetraacetic acid (EDTA) with about 1 mM being preferred. The preferred buffer composition is 10 mM Tris, 10 mM sodium chloride, 1 mM EDTA, pH 8.0 (Tris buffer, pH 8.0). The process can be readily adapted to accommodate larger volumes and/or different numbers of cells by adjusting dilutions and process timing.

The method of this invention can be carried out using a single lytic enzyme but it is preferred that a mixture of such enzymes can be used. The mixture of lytic enzymes to be added to the organism suspension is generally a bacteriolytic enzyme "cocktail" and can include lysozyme, endo-N-acetylmuraminidase and achromopeptidase, among others. The final concentrations of the enzymes in this lytic mixture can be in the range of 50–500 $\mu$g/mL, 10–500 $\mu$g/mL and 50–500 $\mu$g/mL, respectively. The preferred concentrations are 300 $\mu$g/mL, 30 $\mu$g/mL and 300 $\mu$g/mL, respectively.

This lytic enzyme cocktail can be prepared in the Tris buffer, pH 8.0 described above, or any of the generally acceptable buffers can be utilized. This cocktail can be added to the suspension described above at a temperature range of about 20° C.–70° C. and incubated for a time period of about 1–60 minutes. It is known that, in general, enzymatic processes proceed more rapidly at higher temperatures provided the enzyme is not denatured by the higher temperature. It is thus preferred to operate at the highest possible (non-denaturing) temperature for a given enzyme cocktail in order to minimize the time required to complete digestion. This same consideration will apply to all subsequent enzymatic degradation steps. The preferred treatment conditions for the above enzyme mixture are a digestion temperature of about 37° C. for about 10 minutes. Optionally, a reducing agent can be added to the lytic mixture to further improve cell lysis. A variety of reducing agents can be used including dithiothreitol, dithioerythritol, cysteine and ascorbic acid, 2-mercaptoethanol being preferred. The final concentrations of any of the reducing agents can be in the range of 0.1–30 mM. The preferred concentration is 5 mM. To further improve both cell lysis and solubilization, aprotic solvent can be added to the lytic mixture. Among such solvents are N,N-dimethylformamide (DMF) and sulfolane with dimethylsulfoxide (DMSO) being a preferred one. The final concentration of the aprotic solvent can be in the range of 1–20% (v/v). The preferred concentration is 10% (v/v).

The lytic effect of this particular enzyme mixture is broad and includes microorganisms that can be found in the following genera:

| | |
|---|---|
| Aerobacter sp. | Microccocus sp. |
| Acholeplasma sp. | Mycoplasma sp. |
| Achromobacter sp. | Pediococcus sp. |
| Arthrobacter sp. | Proteus sp. |
| Azotobacter sp. | Protaminobacter sp. |
| Bacillus sp. | Pseudomonas sp. |
| Blevibacterium sp. | Salmonella sp. |
| Clostridium sp. | Sarcina sp. |
| Enterobacter sp. | Serratia sp. |
| Escherichia sp. | Shigella sp. |
| Flavobacterium sp. | Staphylococcus sp. |
| Klebsiella sp. | Streptococcus sp. |
| Kurthia sp. | Streptomyces sp. |
| Lactobacillus sp. | |
| Leuconostoc sp. | |

Other enzymes can also be added to the above enzyme cocktail to further broaden its bacteriolytic action. Suitable enzymes include: lipase, lysopeptase, endo-N-acetylglucosaminidase D or H, dextranase, cellulase, glucoamylase, hyaluronidase, N-acetylmuramyl-L-alanine amidase, streptomyces KM endopeptidase, streptomyces SA endopeptidase and streptomyces ML endopeptidase. Such enzymes will generally be useful in concentration ranges from about 10–500 $\mu$g/mL of the mixture. Selection of one or more additional enzymes for inclusion in the lytic cocktail will depend upon the cell wall and cell membrane structure of the cell to be lysed. For example, the streptomyces ML endopeptidase can be added to improve lysis of cells containing type III peptidoglycans. The enzymatic specificity of each of these enzymes is generally known and enzyme selection is expected to be based on the type of organism present.

Complete lysis of the cells can be assured by addition of surfactant to the lytic mixture, increasing the temperature of lysis and/or by using a longer reaction time. The surfactant addition can be prior to, simultaneous with or subsequent to the lytic enzyme treatment. It is generally preferred to add sodium dodecylsulfate (SDS) to a final concentration of about 0.1% (w/v) and to increase the temperature to about 60° C. for 10 minutes. The concentration of SDS can be from about 0.05% to about 1% (w/v); the temperature can range from about 20° C. to about 70° C.; and the time from about 1 minute to about 60 minutes. Other surfactants can be utilized under similar conditions. These include cationic, anionic and nonionic surfactants such as Triton X-100, octyl-$\beta$-D-glucopyranoside, 3-[(3-cholamidopropyl)dimethylammonio]-1-propane sulfonate (CHAPS) and 3-[(3-cholamidopropyl)dimethylammonio]-2-hydroxy-1-propane sulfonate (CHAPSO).

At this stage of the procedure it is necessary to decide whether one wishes to isolate DNA or RNA. Until this stage, the processing does not degrade either DNA or RNA. It is now advantageous to degrade one or the other so that desired nucleic acid can be isolated. Since this invention is expected to have its greatest utility in the isolation of DNA, the remainder of the process will be discussed in terms of DNA isolation and reference will only be made to RNA isolation when specific modifications to the procedure are required.

The RNA in the lysate can be degraded using a ribonuclease (RNase). RNase I A is the preferred enzyme although other RNases such as RNase T, RNase U, RNase H or RNase B can be substituted. The RNase is added to a final concentration of about 50–500 $\mu$g/mL of the lytic mixture at a temperature of about 20° C. to about 70° C. for about 1 to about 60 minutes. The preferred treatment conditions are approximately 300 $\mu$g/mL RNase IA for approximately 10 minutes at approximately 60° C. These conditions serve to degrade rapidly the RNA in the lysate without degrading the DNA. If RNA isolation is desired, digestion with a deoxyribonuclease (DNase) is substituted for RNase digestion. DNase I is a suitable enzyme for use in this manner. In order to avoid degradation of the desired class of nucleic acid, however, it is important to utilize RNase or DNase of appropriate purity.

It is optional, but frequently desirable, at this point to add some Tris buffer, pH 8.0, or water to the lytic mixture to reduce its viscosity. High viscosity can cause reduced recovery of isolated DNA due to inefficient operation of the remaining steps in the process. This optional dilution can be incorporated as part of the RNase treatment step.

The cellular proteins present in the lytic mixture and the RNase can then be degraded with a non-specific protease or a mixture of such broadly active proteases. The preferred protease is Proteinase K, but others such as an alkaline protease isolated from *Streptomyces griseus* can be substituted. The final concentration is preferably 50–500 $\mu$g/mL for about 5–120 minutes at about 20–70° C. A preferred specific treatment condition is approximately 300 $\mu$g/mL of Proteinase K at approximately 60° C. for approximately 30 minutes. This protein degradation step generally replaces the organic solvent extractions of the prior art. By eliminating these extractions, the yield of recoverable DNA can be greatly improved because the extractions expose the DNA to a great deal of shear force and frequently cause the high molecular weight DNA to break into smaller pieces which would be lost during processing. Optionally, a reducing agent can be added to the lytic mixture to further improve the protein degradation. A variety of reducing agents can be used including dithiothreitol, dithioerythritol, cysteine and ascorbic acid, 2-mercaptoethanol being preferred. The final concentrations of any of the reducing agents can be in the range of 1–100 mM. The preferred concentration is 5 mM. To further improve both cell lysis and solubilization, aprotic solvent can be added to the lytic mixture. Among such solvents are N,N-dimethylformamide (DMF) and sulfolane with dimethylsulfoxide (DMSO) being a preferred one. The final concentration of the aprotic solvent can be in the range of 1–50% (v/v). The preferred concentration is 10% (v/v).

Any proteins still associated with nucleic acids or present in the mixture up to this point can be denatured and dissociated from the nucleic acids by the addition of one or more chaotropic agents. By chaotropic agent is meant any substance capable of altering the secondary and tertiary structure of proteins and nucleic acids. The chaotropic agent should be added to the mixture under conditions to avoid denaturation of double-stranded DNA. This means that the temperature of chaotrope treatment should be below approximately 40° C., preferably about 30° C. These lower temperatures are important because double-stranded DNA is more susceptible to heat denaturation when the binding proteins which stabilize it have been degrade, denatured or dissociated from it and because the chaotropic agent can lower the thermal melting temperature of double-stranded DNA. Temperatures as low as about 4° C. can be used. The preferred chaotropic agents are salts such as sodium trifluoroacetate, sodium perchlorate and sodium iodide. The preferred salt is sodium trifluoroacetate at a final concentration of approximately 0.5M, but can range from about 0.1 to about 1.0M. The duration of the chaotrope treatment is about 1–30 minutes with 5 minutes being preferred. In some instances, the contents released from cells during the process of this invention can be of such quantity that the cellular components can precipitate upon the addition of the chaotropic agent reducing the purity and the amount of recovered DNA. Such precipitation can be avoided by adding a buffer, for example, Tris buffer, pH 8.0, or water to the mixture just prior to the addition of the chaotropic agent and/or by using less chaotropic agent.

At this stage, DNA is ready for final purification and concentration. This can be accomplished by collodion membrane dialysis-concentration. Before beginning the dialysis-concentration process, the mixture can be diluted with a low salt buffer such as 10 mM Tris, 1 mM EDTA, pH 8.0 to prevent the concentration process from proceeding too rapidly and causing the cellular components to precipitate. It may be desirable to add more buffer during the concentration process to assure complete removal of contaminants (degradation products of the organisms and the reagents utilized in the process of this invention) before achieving the desired concentration. The concentration process can be stopped when a convenient volume of DNA containing solution remains.

The DNA thus prepared is pure as can be shown by UV spectral analysis. The ratio of the absorbance at 260 nm to that at 280 nm for DNA is between 1.5 and 2. The process of this invention affords products of such a ratio, indicating a high level of purity. Lower ratios are indicative of contamination by proteins and higher ratios indicative of RNA contamination of a DNA preparation.

The purified DNA so obtained is ready for use or can be stored in this form for later use. It is immediately available for restriction endonuclease digestion, molecular weight determination and hybridization analysis, among other uses. Further processing may be necessary for DNA cloning or in recombinant work.

The following examples illustrate the invention. In a method substantially identical to the process described in Examples 1 and 2, genomic DNA was successfully isolated and analyzed from *Klebsiella pneumoniae, Staphylococcus aureus, Enterobacter aerogenes, Proteus mirabilis, E. coli,* and *Staphylococcus epidermis.*

EXAMPLE 1

Isolation and Analysis of Bacterial Genomic DNA from Pseudomonas Aeruginosa

A. DNA Isolation

A cell suspension of *Pseudomonas aeruginosa* DP 295, (ATCC accession number 10145) was prepared by first removing several single colonies from a 37° C. overnight growth on a Petri dish of blood agar base medium with a Pasteur pipet. The cells were then suspended and mixed by vortexing them in 1 mL of 10 mM Tris buffer, pH 8.0, containing 10 mM NaCl and 1 mM EDTA in a 12×75 mm borosilicate glass test tube. A concentration of approximately $3 \times 10^8$ cells/mL was achieved by diluting the cell suspension with the above-mentioned buffer. The cell concentration was determined by a visual comparison of the cell suspension with a McFarland nephelometric turbidity standard of 1 in a 12×75 mm borosilicate glass test tube. 500 μL of this cell suspension was then transferred to another 12×75 mm borosilicate glass test tube for further processing.

A lytic enzyme cocktail was prepared by combining 150 μL of 10 mg/mL lysozyme in water, 150 μL of 10 mg/mL achromopeptidase in water and 150 μL of 1 mg/mL endo-N-acetylmuraminidase in water. This cocktail was stored at −20° C. 45 μL of this cocktail was added to 500 μL of the cell suspension. The mixture was vortexed and incubated at 37° C. for 10 minutes.

5.6 μL of 10% SDS and 15 μL of 10 mg/mL ribonuclease I A in water were added to the tube, vortexed and incubated at 60° C. for 10 minutes.

100 μL of 10 mM Tris buffer, pH 8.0, containing 10 mM NaCl and 1 mM EDTA was added to the tube and vortexed to dilute the sample.

20 μL of 10 mg/mL Proteinase K in water was added to the tube, vortexed and incubated at 60° C. for 30 minutes.

The tube was cooled to 20° C. and to it was slowly added 686 μL if 1M sodium trifluoroacetate that was first filtered with a 0.22 μm Nalgene filter unit. The tube was vortexed and incubated at 20° C. for 5 minutes.

750 μL of TE buffer (10 mM Tris buffer, pH 8.0, containing 1 mM EDTA) was added to the tube and vortexed to dilute the sample.

The sample was then transferred from the test tube into a 2-mL capacity collodion membrane (available from Schleicher & Schuell, Inc. Keene, NH) for dialysis and concentration. The average retention of the collodion membrane was 25,000 Daltons and above. TE buffer, pH 8.0, was used for the dialysis. A vacuum of 19 inches of mercury was used to facilitate the concentration of the sample in a Schleicher & Schuell dialysis and concentration apparatus.

After the sample volume was reduced to approximately 200 μL, the vacuum was released and 500 μL of TE buffer, pH 8.0, was added to the sample and mixed by drawing the ample into a 2 mL glass pipet and expelling it back into the collodion membrane. The dialysate was also removed and replaced with TE buffer, pH 8.0. The dialysis and concentration of the sample was resumed until a final volume of approximately 50 μL was achieved. The purified DNA sample was then removed from the collodion membrane with a Rainin P-200 pipet tip and placed into a 1.5-mL polypropylene Eppendorf tube for storage at 4° C.

B. Restriction Endonuclease Digestion

23 μL of the approximately 50 μL purified DNA sample from above was transferred to another 1.5-mL Eppendorf tube and to it were added: 6 μL of a 5X EcoRI restriction enzyme buffer (500 mM Tris buffer, pH 7.5, containing 50 mM $MgCl_2$, 250 mM NaCl and 500 μg/mL bovine serum albumin from Bethesda Research Laboratories) and 1 μL of 100 units/μL EcoRI restriction endonuclease from Boehringer Mannheim. The tube was gently vortexed and incubated at 37° C. for 4 hours. The reaction was stopped with the addition of 7.5 μL of a 5X Ficoll dye solution (12.5% Ficoll type 400-DL from Sigma, 50 mM EDTA, 0.13% bromphenol blue and 0.13% xylene cyanol).

C. Agarose Gel Electrophoresis

A 0.8% gel was prepared by melting 1.6 g of Seakem LE agarose at 100° C. in 200 mL of a Tris-acetate buffer (20 mM Tris-acetate buffer containing 2 mM EDTA), pH 8.0. The molten agarose was cooled to 50° C. and a gel was cast in a 15×20 cm BioRad electrophoresis tray with a 20 well comb. After the gel cooled to room temperature, the gel was allowed to stand at 4° C. for 1 hour. The comb was removed and the gel was placed into a BioRad submarine gel electrophoresis unit with 1500 mL of Tris-acetate buffer, pH 8.0, at room temperature. 30 μL of the DNA-ficoll dye containing solution was added to a well in the agarose gel. The electrophoretic separation of the DNA fragments was then allowed to proceed for 15 hours at 1.5 volts/cm with the buffer circulating in the unit at 250 mL/hour.

D. Transfer of Size-Separated DNA Fragments onto a Membrane Support

An electroblotting method was used. The DNA fragments in the gel were first denatured in 700 mL of 0.4N sodium hydroxide at room temperature for 30 minutes with a gently rocking motion. The gel was then treated for 5 minutes in 700 mL of electroblot buffer (12 mM Tris buffer, pH 7.5, containing 6 mM sodium acetate and 0.3 mM EDTA). The electrophoretic transfer of the denatured DNA fragments from the gel onto a membrane support (electroblotting) was carried out using a Hoefer TE 42 Transphor Electrophoresis Cell. To prepare the gel for electroblotting, one side of the Hoefer Transphor Cassette was submerged in an 8-L polypropylene tray containing 3 L of electroblot buffer, pH 7.5, at room temperature. A 15.5×22 cm Dacron ® polyester fiber sponge (a registered trademark of E .I. du Pont de Nemours and Company) was placed on top of the inside surface of the Transphor Cassette and layered with the following materials: 1 sheet of 15×21.5 cm blotter paper, a piece of charged modified nylon membrane (GeneScreen ™ Plus, available from E. I. du Pont de Nemours and Company) cut to the same size as the gel, the agarose gel with the denatured DNA fragments and 2 sheets of 15×21.5 cm blotter paper. To finish the assembly of the Transphor Cassette, the Dacron ® polyester sponge/blotter paper/agarose gel/blotter paper sandwich was locked between the tow sides of the Transphor Cassette and placed into a Transphor Cell containing 4.5 L of electroblot buffer, pH 7.5, chilled to 5° C. The operation of the Transphor Cell was carried out at 2 different voltage settings as follows: first at 10 volts for 60 minutes and then at 40 volts for 60 minutes. A temperature of 5° C. was maintained throughout the entire operation of the Transphor Cell. The membrane was then removed from the Transphor Cassette, rinsed in electroblot buffer, pH 7.5, and air dried for 30 minutes at room temperature.

E. DNA Probe Preparation

Plasmid DNA [pKK3535, Brosius et al., Plasmid, Volume 6, 112–118 (1981)], known to contain DNA sequences which are capable of hybridizing with those portions of the genomic DNA which code for rRNA, was labeled with $^{32}P$ for use as a DNA probe using a Nick-translation Kit (available from E. I. du Pont de Nemours and Company). The following were added to a 1.5-mL Eppendorf tube: 9 μL of 550 μg/mL plasmid DNA; 61 μL of water, 50 μL of nick-translation buffer; 40 μL of a solution containing dATP, dGTP, and dTTP: 1 millicurie of $^{32}P$-dCTP with a specific activity of 3000 Curies/mmole in a volume of 100 μL; 20 μL of DNA polymerase I; and 20 μL of DNase I. The contents were mixed by drawing them into a Rainin P-200 pipet tip and expelling them back into the tube. The reaction was then allowed to proceed at 15° C. for 60 minutes. The reaction was stopped with the addition of 6 μL of 500 mM EDTA. The $^{32}P$-labeled probe DNA was then separated from the unincorporated deoxynucleotide triphosphates by size separation on a 0.7×30 cm Sephadex G-50 column with TE buffer, pH 8.0. The specific activity of the labeled doublestranded DNA probe was approximately $3 \times 10^8$ dpm/μg DNA.

F. DNA Probe Hybridization

The hybridization membrane containing the transferred DNA fragments (prepared in step D above) was pre-hybridized with 100 μg/mL sonicated, denatured, salmon sperm DNA for 30 minutes in 200 mL of 3X SSC buffer (3X SSC buffer contains 0.45M NaCl and 0.045M sodium citrate), containing 0.5% SDS, 10X Denhardt's solution (10X Denhardt's solution contains 0.2% ficoll, 0.2% polyvinylpyrolidone and 0.2% bovine serum albumin, fraction 5), at 60° C. in a sealed plastic box on a rocker platform. The purified $^{32}P$-labeled DNA probe was then denatured by heating it to 100° C. in a boiling water bath for 5 minutes, quickly cooled to 4° C. on ice and added immediately to the pre-hybridization mix on the membrane to achieve approximately $4 \times 10^6$ dpm/mL. Hybridization was allowed to proceed for 20 hours at 60° C. with continuous rocking. After 20 hours, any unreacted $^{32}P$-labeled DNA probe was removed by four successive 15-minute washes with 3X SSC buffer containing 0.5% SDS at 60° C. with continuous rocking. The membrane was then removed from the wash solution and air dried at room temperature.

G. Analysis of the Restriction Fragment Length Polymorphisms

The ribosomal RNA operon(s) contained between the EcoRl restriction sites of the genomic DNA were detected by visualization of the labeled hybrids by autoradiography of the membrane on x-ray film. The same fragment sizes and number of fragments were observed from the Pseudonomas aeruginosa cells as have previously been obtained by using the DNA isolation method of De Klowet with phenol/chloroform extractions and alcohol precipitations.

EXAMPLE 2

Isolation and Analysis of Bacterial Genomic DNA From Streptococcus Faecalis

A. DNA Isolation

A cell suspension of *Streptococcus Faecalis* DP 283 (ATCC accession number 19433) was prepared by first removing several single colonies from a 37° C. overnight growth on a Petri dish of blood agar base medium with a Pasteur pipet. The cells were then suspended and mixed by vortexing them in 1 mL of 10 mM Tris buffer, pH 8.0, containing 10 mM NaCl and 1 mM EDTA in a 12×75 mm borosilicate glass test tube. A concentration of approximately $6 \times 10^8$ cells/mL was achieved by diluting the cell suspension with the above-mentioned buffer. The cell concentration was determined by a visual comparison of the cell suspension with a McFarland nephelometric turbidity standard of 2 in a 12×75 mm borosilicate glass test tube. 500 μL of this cell suspension was then transferred to another 12×75 mm borosilicate glass test tube for further processing.

45 μL of the lytic enzyme cocktail prepared in Example 1(A) was added to 500 μL of the cell suspension. The mixture was vortexed and incubated at 37° C. for 10 minutes. 5.6 μL of 10% SDS was added to the tube, vortexed and incubated at 60° C. for 10 minutes.

15 μL of 10 mg/mL ribonuclease I A in water was added to the tube, vortexed and incubated at 60° C. for 10 minutes.

100 μL of 10 mM Tris buffer, pH 8.0, containing 10 mM NaCl and 1 mM EDTA was added to the tube and vortexed to dilute the sample.

20 μL of 10 mg/mL Proteinase K in water was added to the tube, vortexed and incubated at 60° C. for 30 minutes.

The tube was cooled to 20° C. and to it was slowly added 686 μL of 1M sodium trifluoroacetate that was first filtered with a 0.22 μm Nalgene filter unit. The tube was vortexed and incubated at 20° C. for 5 minutes.

750 μL of TE buffer was added to the tube and vortexed to dilute the sample.

The sample was then transferred from the test tube into an 8-mL capacity Schleicher & Schuell collodion membrane, average retention of above 75,000 Daltons, for dialysis and concentration. TE buffer, pH 8.0, was used for the dialysis. A vacuum of 19 inches of mercury was used to facilitate the concentration of the sample in a Schleicher & Schuell flatbottom apparatus. A magnetic stirring bar was used inside of the apparatus to facilitate mixing of the dialysis buffer during the process.

After the sample volume was reduced to approximately 200 μL, the vacuum was released and 500 μL of TE buffer, pH 8.0, was added to the sample and mixed by drawing the sample into a 2-mL glass pipet and expelling it back into the collodion membrane. The dialysate was also removed and replaced with TE buffer, pH 8.0. The dialysis and concentration of the sample was resumed until a final volume of approximately 50 μL was achieved. The purified DNA sample was then removed from the collodion membrane with a Rainin P-200 pipet tip and placed into a 1.5-mL polypropylene Eppendorf tube for storage at 4° C.

Steps (B) through (F) were carried out as described in Example 1(B) through (F).

G. Analysis of the Restriction Fragment Length Polymorphisms

The ribosomal RNA operon(S) contained between the EcoRI restriction sites of the genomic DNA were detected by visualization of the labeled hybrids by autoradiography of the membrane on x-ray film. The same fragment sizes and number of fragments were observed from the *Streptococcus faecalis* cells as have previously been obtained by using the DNA isolation method of De Klowet with phenol/chloroform extractions and alcohol precipitations.

EXAMPLE 3

Isolation and Analysis of Bacterial DNA

A. DNA Isolation

An unamplified cell suspension of *Escherichia coli* K12 strain LM1035 containing the plasmid pKK3535 [Brosius et al. Plasmid, Volume 6, 112–118 (1981)] was prepared by first removing several single colonies from a 37° C. overnight growth on a Petri dish of trypticase soy agar containing 100 μg/mL ampicillin with pasteur pipet. The cells were then suspended and mixed by vortexing them in 1 mL of 10 mM Tris buffer, pH 8.0, containing 10 mM NaCl and 1 mM EDTA in a 12×75 mm borosilicate glass test tube. A concentration of approximately $3 \times 10^8$ cells/mL was achieved by diluting the cell suspension with the above-mentioned buffer. The cell concentration was determined by a visual comparison of the cell suspension with a McFarland nephelometric turbidity standard of 1 in a 12×75 mm borosilicate glass test tube. 500 μL of this cell suspension was then transferred to another 12×75 mm borosilicate glass test tube for further processing.

45 μL of the lytic enzyme cocktail prepared in Example 1(A) was added to 500 μL of the cell suspension in a test tube. The mixture was vortexed and incubated at 37° C. for 10 minutes.

5.6 μL of 10% SDS and 15 μL of 10 mg/mL ribonuclease I A in water were added to the tube, vortexed and incubated at 60° C. for 10 minutes.

100 μL of 10 mM Tris buffer, pH 8.0, containing 10 mM NaCl and 1 mM EDTA was added to the tube and vortexed to dilute the sample.

20 μL of 10 mg/mL Proteinase K in water was added to the tube, vortexed and incubated at 60° C. for 30 minutes.

The tube was cooled to 20° C. and to it was slowly added 686 μL of 1M sodium trifluoroacetate that was first filtered with a 0.22 μm Nalgene filter unit. The tube was vortexed and incubated at 20° C. for 5 minutes.

750 μL of TE buffer was added to the tube and vortexed to dilute the sample.

The sample was then transferred from the test tube into an 8-mL capacity Schleicher & Schuell collodion membrane for dialysis and concentration. The average retention of the collodion membrane was 75,000 Dalons and above. TE buffer, pH 8.0, was used for the dialysis. A vacuum of 19 inches of mercury was used to facilitate the concentration of the sample in the Schleicher & Schuell flat-bottom apparatus.

After the sample volume was reduced to approximately 200 μL, the vacuum was released and 500 μL of TE buffer, pH 8.0, was added to the sample and mixed by drawing the sample into a 2-mL glass pipet and expelling it back into the collodion membrane. The dialysate was also removed and replaced with TE buffer, pH 8.0. The dialysis and concentration of the sample was resumed until a final volume of approximately 50 μL was achieved. The purified DNA sample so obtained was then removed from the collodion membrane with a Rainin P-200 pipe tip and placed into a 1.5-mL polypropylene Eppendorf tube for storage at 4° C.

B. Agarose Gel Electrophoresis

Electrophoresis was carried out as described in Example 1(B) with the following modifications:

6 μL of a 5X Ficoll dye solution (12.5% Ficoll type 400-DL from Sigma, 50 mM EDTA, 0.13% bromphenol blue and 0.13% xylene cyanol) was added to 25 μL of the purified DNA sample in an Eppendorf tube and gently vortexed. 30 μL of the DNA-ficoll dye containing solution was then added to a well in the agarose gel. The electrophoretic separation of the DNA was then allowed to proceed for 2 hours at 3 volts/cm with the buffer circulating in the unit at 250 mL/hour.

C. Plasmid DNA Detection

The presence of plasmid DNA in *E. coli* was ascertained by exposing the gel to ultraviolet light, 302 nm, and by observing the fluorescence of the nucleic acids. Proof of the presence of the plasmid pKK3535 was obtained by photographing the fluorescent nucleic acids and observing a band corresponding to the molecular weight of the plasmid. The results of this Example 3 demonstrate that the process of this invention is useful for isolation of intact plasmid DNA also.

I claim:

1. A method of isolating nucleic acids from their source organism comprising the steps of:
   (A) forming a suspension of said organism containing or suspected of containing the desired nucleic acid;
   (B) treating said organism with a cocktail of lytic enzymes;
   (C) treating said organism with surfactant prior to, simultaneously with or subsequent to step (B);
   (D) degrading unwanted classes of nucleic acids by treatment with nucleases specific for the unwanted nucleic acids; then
   (E) degrading proteins by digestion with at least one broadly active protease;
   (F) denaturing remaining proteins and dissociating them from the nucleic acid by adding at least one chaotropic agent; and then
   (G) dialyzing and concentrating the nucleic acid.

2. The method of claim 1 wherein the source organism is selected from the group consisting of cells and viruses.

3. The method of claim 2 wherein said cells are microorganisms.

4. The method of claim 1 wherein the mixture of lytic enzymes comprises lysozyme, endo-N-acetylmuraminidase and achromopeptidase.

5. The method of claim 1 wherein the nucleases are RNases.

6. The method of claim 1 wherein the nucleases are DNases.

7. The method of claim 1 wherein the chaotropic agent is selected from the group consisting of sodium trifluoroacetate, sodium perchlorate and sodium iodide.

8. A method of isolating DNA from cells or viruses comprising the steps of:
   (A) forming a suspension of said cells or viruses containing or suspected of containing the desired DNA;

(B) treating said cells or viruses with a mixture of lytic enzymes comprising lysozyme, endo-N-acetylmuraminidase and achromopeptidase;
(C) treating said cells or viruses with sodium dodecyl sulfate;
(D) degrading RNA from said cells or viruses with RNases; then
(E) degrading proteins by digestion with Proteinase K;
(F) denaturing remaining proteins and dissociating them from DNA by adding chaotropic salt; and then
(G) dialyzing and concentrating the DNA.

* * * * *